(12) United States Patent
Liu et al.

(10) Patent No.: US 11,865,196 B2
(45) Date of Patent: Jan. 9, 2024

(54) ENGINEERED RADIOACTIVE POLYMERIC MICROSPHERE, AND PREPARATION AND APPLICATION THEREOF

(71) Applicants: Xiamen University, Xiamen (CN); Shanghai University, Shanghai (CN)

(72) Inventors: Gang Liu, Xiamen (CN); Xiao Xu, Xiamen (CN); Hongjuan Ma, Shanghai (CN); Zhenwen Zhao, Xiamen (CN); Hu Chen, Xiamen (CN); Pan He, Xiamen (CN); Chao Liu, Xiamen (CN); Chengchao Chu, Xiamen (CN); Dong Li, Xiamen (CN)

(73) Assignees: Xiamen University, Xiamen (CN); Shanghai University, Shanghai (CN)

( * ) Notice: Subject to any disclaimer, the term of this patent is extended or adjusted under 35 U.S.C. 154(b) by 0 days.

(21) Appl. No.: 18/339,195

(22) Filed: Jun. 21, 2023

(65) Prior Publication Data
US 2023/0346992 A1 Nov. 2, 2023

(51) Int. Cl.
| | | |
|---|---|---|
| *A61P 35/00* | (2006.01) | |
| *A61K 51/12* | (2006.01) | |
| *C08F 257/02* | (2006.01) | |
| *C08K 3/06* | (2006.01) | |
| *A61N 5/10* | (2006.01) | |

(52) U.S. Cl.
CPC ........ *A61K 51/1251* (2013.01); *A61N 5/1002* (2013.01); *A61P 35/00* (2018.01); *C08F 257/02* (2013.01); *C08K 3/06* (2013.01); *A61N 2005/1021* (2013.01)

(58) Field of Classification Search
CPC ........ A61K 51/1251; A61P 35/00; C08K 3/16
See application file for complete search history.

(56) References Cited

U.S. PATENT DOCUMENTS

| | | | |
|---|---|---|---|
| 5,306,561 A | 4/1994 | Frechet et al. | |
| 2004/0258614 A1 | 12/2004 | Line et al. | |
| 2015/0273089 A1* | 10/2015 | Gray | A61P 35/00 |
| | | | 424/1.29 |

FOREIGN PATENT DOCUMENTS

| | | |
|---|---|---|
| CN | 103788301 A | 5/2014 |
| CN | 109265613 A | 1/2019 |
| CN | 113018463 A | 6/2021 |
| EP | 3031472 A1 | 6/2016 |
| JP | 2013212484 A | 10/2013 |
| JP | 2016075655 A | 5/2016 |
| WO | 2022042279 A1 | 3/2022 |

OTHER PUBLICATIONS

Tianzhi Tan Ed. "Clinical Nuclear Medicine", People's Medical Publishing House, Nov. 30, 1993, p. 183.

* cited by examiner

*Primary Examiner* — Michael G. Hartley
*Assistant Examiner* — Jagadishwar R Samala (57) ABSTRACT

An engineered radioactive polymeric microsphere, and a preparation and application thereof. The preparation method includes: adding a styrene monomer and a disperser and/or a crosslinker into a medium, followed by feeding of nitrogen or helium and stirring to obtain a first reaction mixture; heating the first reaction mixture, and adding an initiator, followed by reaction under stirring at a constant temperature to obtain a second reaction mixture; subjecting the second reaction mixture to washing with ethanol and water, and vacuum drying to obtain a crude polymeric microsphere; subjecting the crude polymeric microsphere to radiation-induced graft polymerization with a functional monomer to obtain the functionalized polymeric microsphere; and exposing the functionalized polymeric microsphere to a radionuclide to prepare the engineered radioactive polymeric microsphere.

3 Claims, 3 Drawing Sheets

ENGINEERED RADIOACTIVE POLYMERIC MICROSPHERE, AND PREPARATION AND APPLICATION THEREOF

CROSS-REFERENCE TO RELATED APPLICATIONS

This application claims the benefit of priority from Chinese Patent Application No. 202210736748.2, filed on Jun. 27, 2022. The content of the aforementioned application, including any intervening amendments thereto, is incorporated herein by reference in its entirety.

TECHNICAL FIELD

This application relates to pharmaceutical technology, and more particularly to an engineered radioactive polymeric microsphere, and a preparation and application thereof.

BACKGROUND

Regarding the brachytherapy involving the intravascular injection of radioactive microspheres, the radionuclide-loaded microspheres are delivered into a blood vessel supplying the tumors through catheter intervention, such that the radionuclide can accumulate to a therapeutically-effective dose in the tumor tissue to kill tumor cells via brachytherapy. Such therapy strategy has been increasingly used for the diagnosis and treatment of primary liver cancer that is unresectable, or is not suitable to be treated by liver transplantation. There are already some commercially-available radioactive microspheres, for example, TheraSphere™ Yttrium-90 (Y-90) Glass Microspheres developed by Boston Scientific Corporation has been approved by U.S. Food and Drug Administration (FDA) for the treatment of unresectable hepatocellular carcinoma (HCC); SIR-Spheres® Y-90 Resin Microspheres designed by Sirtex Medical are indicated for the radiotherapy of the unresectable metastatic liver tumor from the primary colorectal cancer, and have also received FDA approval for the treatment of primary liver cancer in March 2021 (dosing of the first patient in clinical trial of the SIR-Spheres® Y-90 Resin Microspheres for the treatment of primary liver cancer has been announced in May 2021); and Quirem Medical B.V. has also received Conformité Européenne (CE) approval for $^{166}$Ho Poly-L-lactic Acid Microspheres, developed for the treatment of unresectable primary and secondary hepatocellular carcinoma via single-photon emission computerized tomography (SPECT).

Unfortunately, although these radioactive microspheres have exhibited a certain clinical efficacy, they are still struggle with some shortcomings. For example, the Y-90 glass microspheres and the $^{166}$Ho poly-L-lactic acid microspheres are prepared by neutron activation, which requires a nuclear reactor, thereby leading to high costs. Moreover, this process is often accompanied by the occurrence of unwanted long-lived radioisotope due to impurities in the glass microspheres (such as alumina and silica), and the glass microspheres are prone to depositing in the proximal blood vessels of the tumor since the density of glass microspheres is much higher than that of blood, resulting in poor injectability, and non-uniform distribution in the tumor lesion. Although the Y-90 resin microspheres do not involve the above-mentioned problems, they are poor in radiolabeling stability, such that the radionuclide will be easily released from the microspheres. Therefore, it is required to disperse the Y-90 resin microspheres in deionized water for use, which may lead to pain, vasospasm, vascular endothelial cell damage and premature arterial stasis. Recently, the administration of Y-90 resin microspheres have been optimized by catheter intervention with 5% glucose and contrast agent, however, the Y-90 loaded on the resin microspheres may be replaced with ions in the tissue fluid, which leads to the loss and wide distribution in major organs, thereby resulting in adverse reactions such as bone marrow suppression and radiation pneumonia complications.

Therefore, it is urgent to provide a radioactive microsphere with excellent therapeutic efficacy, high stability and safety, uniform distribution and low cost.

SUMMARY

In order to overcome the above-described problems in the prior art, the present disclosure provides an engineered radioactive polymeric microsphere, and a preparation and application thereof.

The technical solutions of the present disclosure are described as follows.

In a first aspect, the disclosure provides a method for preparing a functionalized polymeric microsphere, comprising:
  adding a styrene monomer and at least one of a disperser and a crosslinker into a medium, followed by feeding of nitrogen or helium and stirring to obtain a first reaction mixture;
  heating the first reaction mixture and adding an initiator to the first reaction mixture, followed by reaction under stirring at a constant temperature to obtain a second reaction mixture;
  subjecting the second reaction mixture to washing with ethanol and water, and vacuum drying to obtain a crude polymeric microsphere; and
  subjecting the polymeric microsphere to radiation-induced graft polymerization with a functional monomer to obtain the functionalized polymeric microsphere.

In some embodiments, the crosslinker is selected from the group consisting of vinyl toluene, divinyl benzene, trivinyl benzene, and a combination thereof; and the medium is selected from the group consisting of deionized water, ethanol, methanol, and a combination thereof.

In some embodiments, the initiator is selected from the group consisting of azobisisobutyronitrile, dibenzoyl peroxide, cyclohexanone peroxide, and a combination thereof.

In some embodiments, the functional monomer is selected from the group consisting of N-vinyl-2-pyrrolidone, vinylphosphonic acid, 2-methacryloyloxyethyl phosphorylcholine, itaconic acid, phenyl vinylsulfonate, ethyl styrenesulfonate, and a combination thereof.

In a second aspect, the disclosure provides a functionalized polymeric microsphere prepared by the above-mentioned method.

In a third aspect, the disclosure provides a method for preparing an engineered radioactive polymeric microsphere, comprising:
  exposing the functionalized polymeric microsphere of claim 5 to a radionuclide to allow the radionuclide to be adsorbed on the functionalized polymeric microsphere, so as to prepare the engineered radioactive polymeric microsphere.

In some embodiments, the radionuclide is holmium-166 ($^{166}$Ho), rhenium-188 ($^{188}$Re), lutetium-177 ($^{177}$Lu), yttrium-90 ($^{90}$Y) or copper-64 ($^{64}$Cu).

In a fourth aspect, the disclosure provides an engineered radioactive polymeric microsphere prepared by the above-mentioned method.

In a fifth aspect, the disclosure provides a drug for intravascular brachytherapy of a tumor, comprising:
the above-mentioned engineered radioactive polymeric microsphere.

In a sixth aspect, the disclosure provides a method for interventional radiotherapy of cancer in a subject in need thereof, comprising:
administering a therapeutically-effective amount of the above-mentioned engineered radioactive polymeric microsphere to the subject.

Compared to the prior art, this application has the following beneficial effects.

The functionalized polymeric microsphere provided herein can undergo specific complexation with the radionuclide. In addition, it has a diameter of 10-300 μm, and a specific weight of 1.05-1.25 g/mL which is close to the specific weight of blood (1.05 g/mL), contributing to a more uniform distribution in blood.

Based on the combination of radiation-induced graft polymerization and emulsion-suspension polymerization, the functionalized polymeric microsphere prepared herein has great physico-chemical structural stability, and can resist pH environment of tissue fluid and acidic tumor microenvironment, and thus the nuclide release rate is extremely low. Therefore, the functionalized polymeric microsphere designed herein is suitable for the intravascular brachytherapy of tumors.

An adsorption rate of the functionalized polymeric microsphere for $^{177}$Lu or $^{166}$Ho reaches 95.8% or more. The in-vitro nuclide release rate of the functionalized polymeric microsphere loaded with $^{177}$Lu or $^{166}$Ho is much lower than 0.01%.

The functionalized polymeric microsphere and the engineered radioactive polymeric microsphere provided herein have excellent biocompatibility, and are safe and non-toxic. Such radioactive polymeric microspheres varying in particle size can be used for transarterial radioembolization (TARE) combined with immunotherapy for hypervascular tumors such as liver tumor, or used in the treatment of lymphatic tumors and lymphatic metastatic tumors.

The functionalized polymeric microsphere and the engineered radioactive polymeric microsphere provided herein have simple preparation, low cost, and excellent industrial applicability, and thus exhibit a brilliant clinical application prospect, and great economic benefit.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The accompanying drawings needed in the description of the embodiments of the disclosure will be briefly described below to explain the technical solutions of the present disclosure more clearly. Obviously, presented in the accompany drawings are merely some embodiments of the present disclosure, which are not intended to limit the disclosure. Other drawings can be obtained by those skilled in the art based on the drawings provided herein without paying creative effort.

DETAILED DESCRIPTION OF EMBODIMENTS

The disclosure will be described completely and clearly below with reference to the accompanying drawings and embodiments to make the object, technical solutions, and beneficial effects of the present disclosure clearer. Obviously, provided below are merely some embodiments of the disclosure, which are not intended to limit the disclosure. Therefore, the embodiments provided in the accompanying drawings are merely illustrative, and are not intended to limit the scope of the present disclosure. Based on the embodiments of the present disclosure, all other embodiments obtained by those skilled in the art without paying any creative effort shall fall within the scope of the present disclosure.

In addition, terms, such as "first" and "second", are illustrative, and should not be understood as indicating or implying a relative importance or the number of elements referred to. Therefore, the elements defined with "first" and "second" may explicitly or implicitly include at least one of the element. Unless otherwise specified, term "a plurality of" means two or more.

This application provides a method for preparing a functionalized polymeric microsphere, which includes the following steps.

A styrene monomer and a disperser and/or a crosslinker are added into a medium and stirred under the nitrogen or helium supply to obtain a first reaction mixture. The first reaction mixture is heated, added with an initiator and subjected to reaction under stirring at a constant temperature to obtain a second reaction mixture. The second reaction mixture is subjected to washing with ethanol and water (preferably 60° C.), and vacuum drying to obtain a crude polymeric microsphere. The crude polymeric microsphere is subjected to pre-irradiation, and graft polymerization with one or more functional monomers to obtain the functionalized polymeric microsphere. The functionalized polymeric microsphere prepared by the combination of radiation-induced graft polymerization and emulsion-suspension polymerization has great physico-chemical structural stability.

In an embodiment, the crosslinker is selected from the group consisting of vinyl toluene, divinyl benzene, trivinyl benzene, and a combination thereof; and the medium is selected from the group consisting of deionized water, ethanol, methanol, and a combination thereof.

In an embodiment, the disperser is sodium dodecyl sulfate (SDS).

In an embodiment, the initiator is selected from the group consisting of azobisisobutyronitrile, dibenzoyl peroxide, cyclohexanone peroxide, and a combination thereof.

In an embodiment, the functional monomer is selected from the group consisting of N-vinyl-2-pyrrolidone, vinylphosphonic acid, 2-methacryloyloxyethyl phosphorylcholine, itaconic acid, phenyl vinylsulfonate, ethyl styrenesulfonate, and a combination thereof.

In an embodiment, the reaction to obtain the second reaction mixture is performed at 40-90° C. for 5.5-6.5 h.

In an embodiment, the radiation-induced graft polymerization is performed through the following steps. The polymeric microsphere is subjected to pre-irradiation to obtain a pre-irradiated polymeric microsphere. An irradiated monomer aqueous solution is prepared by mixing the functional monomer with water. The pre-irradiated polymeric microsphere is added into the irradiated monomer aqueous solution for reaction to obtain the functionalized polymeric microsphere.

Alternatively, an irradiated monomer aqueous solution is prepared by mixing the functional monomer with water. The polymeric microsphere is added into the irradiated monomer aqueous solution for graft polymerization by simultaneous irradiation to obtain the functionalized polymeric microsphere.

In an embodiment, when an irradiation source of the pre-irradiation is an electron beam accelerator, the pre-irradiation is performed by an electron beam, and an irradiation dose is 50-500 kGy. For example, the polymeric microsphere is exposed to a cobalt source irradiation source with an irradiation dose of 80-600 kGy for the pre-irradiation.

A functionalized polymeric microsphere is provided, which is prepared by the above-mentioned method, and has a diameter of 10-300 μm.

This application provides a method for preparing an engineered radioactive polymeric microsphere, which includes the following steps.

The functionalized polymeric microsphere absorbs a radionuclide to prepare the engineered radioactive polymeric microsphere. The functionalized polymeric microsphere is mixed with a radionuclide solution for a while, such that the functionalized polymeric microsphere can absorb the radionuclide.

In an embodiment, the radionuclide is $^{166}$Ho, $^{188}$Re, $^{177}$Lu, $^{90}$Y or $^{64}$Cu. Preferably, the radionuclide is $^{177}$Lu or $^{166}$Ho. $^{177}$Lu can emit β-particle with three types of energy and has low particle energy, and a tissue penetration distance of one or more millimeters. $^{177}$Lu has small radiation effect on peripheral normal tissues, and the half-life thereof is 6.7 days. A required initial specific activity for clinical use of $^{177}$Lu is much lower than that of $^{90}$Y and $^{188}$Re which have a short half-life, thus beneficial to radiation protection and public health. $^{177}$Lu also emits γ rays (113 keV (6.4%) and 208 keV (11%)), facilitating to in vivo localization imaging and integration of tumor diagnosis and treatment. A maximum energy of β-particle emitted by $^{166}$Ho is 1.85 MeV (50.0%) and 1.77 MeV (48.7%). A tissue penetration distance of $^{166}$Ho is 2.5 mm (up to 8.7 mm). In addition, $^{166}$Ho also emits low-energy γ rays (81 KeV), has half-life of 26.8 h, and more than 90% specific activity can be released within 4 days after the interventional administration.

In an embodiment, the radionuclide solution is a $^{177}$LuCl$_3$ solution or a $^{166}$HoCl$_3$ solution.

An engineered radioactive polymeric microsphere prepared by the above-mentioned method is also provided.

The application provides a drug for intravascular brachytherapy of a tumor, which includes the engineered radioactive polymeric microsphere. A radioactive activity of $^{177}$Lu or $^{166}$Ho is 0.74 GBq-3.70 GBq (20 mCi-100 mCi).

This application provides a use of the engineered radioactive polymeric microsphere in preparation of a drug for interventional radiotherapy of cancer. The drug is for trans-arterial radioembolization (TARE), or is an embolic agent of TAE.

Provided below are merely some embodiments of the disclosure, which are not intended to limit the disclosure.

Example 1 Preparation of Engineered Radioactive Polymeric Microsphere (S1) To 20 mL of deionized water were added 10 g of a styrene monomer and 1 g of sodium dodecyl sulfate (SDS). The reaction mixture was stirred at room temperature for 2 h under a nitrogen atmosphere, heated to 50° C., and added with 2 g of dibenzoyl peroxide. The reaction mixture was reacted under stirring at a constant temperature for 6 h, washed with ethanol and 60° C. water, and dried under vacuum to obtain a crude polymeric microsphere.

(S2) 3 g of the crude polymeric microsphere was exposed to a cobalt source at room temperature under an air atmosphere to undergo a pre-irradiation to obtain a pre-irradiated polymeric microsphere, where a radiation absorbed dose was 100 kGy. To a conical flask were added 60 mL of deionized water and 10 mL of vinylphosphonic acid, which were stirred evenly for 1 h, added with 3 g of the pre-irradiated polymeric microsphere, fed with nitrogen for 20 min to remove oxygen, and then sealed. The reaction system was reacted in a 55° C. water bath for 3 h, and subjected to vacuum filtration to obtain a grafted polymeric microsphere. The grafted polymeric microsphere was washed with deionized water, and dried in a vacuum oven for 24 h to obtain a phosphate-based polymeric microsphere.

(S3) 0.5 g of the phosphate-based polymeric microsphere and 1 mL of a 0.5 mCi/μL $^{177}$LuCl$_3$ solution were mixed at room temperature under ultrasonic oscillation for 30 min to obtain an engineered phosphate-based $^{177}$Lu polymeric microsphere with a diameter of 40 μm.

By means of an intra-arterial catheter or a syringe, the active-targeting delivery of the engineered phosphate-based $^{177}$Lu polymeric microsphere to a tumor lesion can be achieved.

Example 2 Preparation of Engineered Radioactive Polymeric Microsphere (S1) To 50 mL of ethanol were added with 20 g of a styrene monomer and 3 g of SDS. The reaction mixture was stirred at room temperature for 1 h under a helium atmosphere, heated to 60° C., and added with 0.5 g of azobisisobutyronitrile. The reaction mixture was reacted under stirring at a constant temperature for 4 h, washed with ethanol and 60° C. water, and dried under vacuum to obtain a crude polymeric microsphere.

(S2) 5 g of the crude polymeric microsphere were exposed in an electron beam at room temperature under an air atmosphere to undergo a pre-irradiation to obtain a pre-irradiated polymeric microsphere, where a radiation absorbed dose was 300 kGy. To a conical flask were added 50 mL of deionized water, 10 mL of vinyl pyrrolidone and 15 mL of 4-vinylaniline, which were stirred evenly for 2 h, added with 4 g of the pre-irradiated polymeric microsphere, fed with nitrogen for 40 min to remove oxygen, and then sealed. The reaction system was reacted in a 65° C. water bath for 6 h, and subjected to vacuum filtration to obtain a grafted polymeric microsphere. The grafted polymeric microsphere was washed with deionized water, and dried in a vacuum oven for 24 h to obtain an amino-based polymeric microsphere.

(S3) 2 g of the amino-based polymeric microsphere and 1 mL of a 0.5 mCi/μL $^{177}$LuCl$_3$ solution were mixed at room temperature under ultrasonic oscillation for 30 min to obtain an engineered amino-based $^{177}$Lu polymeric microsphere with a diameter of 80 μm.

By means of an intra-arterial catheter or a syringe, the active-targeting delivery of the engineered amino-based $^{177}$Lu polymeric microsphere to a tumor lesion can be achieved.

Example 3 Preparation of Engineered Radioactive Polymeric Microsphere (S1) To 80 mL of deionized water were added 12 g of a styrene monomer and 4 g of SDS. The reaction mixture was stirred at room temperature for 1 h under a nitrogen atmosphere, heated to 50° C., and added with 1.2 g of azobisisobutyronitrile. The reaction mixture was reacted under stirring at a constant temperature for 3 h, washed with ethanol and 60° C. water, and dried under vacuum to obtain a crude polymeric microsphere.

(S2) 4 g of the crude polymeric microsphere were exposed to an electron beam at room temperature under an air atmosphere to undergo a pre-irradiation to obtain a pre-irradiated polymeric microsphere, where a radiation absorbed dose was 200 kGy. To a conical flask were added 50 mL of deionized water, 10 mL of acrylic acid and 10 g of 2-methacryloyloxyethyl phosphorylcholine, which were stirred evenly for 2 h, added with 2 g of the pre-irradiated polymeric microsphere, fed with nitrogen for 30 min to remove oxygen, and then sealed. The reaction system was reacted in a 60° C. water bath for 5 h, and subjected to vacuum filtration to obtain a grafted polymeric microsphere. The grafted polymeric microsphere was washed with deionized water, and dried in a vacuum oven for 24 h to obtain a carboxyl-phosphorylcholine-based polymeric microsphere.

(S3) 1.2 g of the carboxyl-phosphorylcholine-based polymeric microsphere and 2 mL of a 0.5 mCi/μL $^{177}$LuCl$_3$ solution were mixed at room temperature under ultrasonic oscillation for 30 min to obtain an engineered carboxyl-phosphorylcholine-based $^{177}$Lu polymeric microsphere with a diameter of 60 μm.

By means of an intra-arterial catheter or a syringe, the active-targeting delivery of the engineered carboxyl-phosphorylcholine-based $^{177}$Lu polymeric microsphere to a tumor lesion can be achieved.

Example 4 Preparation of Engineered Radioactive Polymeric Microsphere (S1) To 65 mL of deionized water were added 13 g of a styrene monomer, 5 g of SDS and 2 g of divinylbenzene. The reaction mixture was stirred at room temperature for 0.5 h under a nitrogen atmosphere, heated to 70° C., and added with cyclohexanone peroxide. The reaction mixture was reacted under stirring at a constant temperature for 4 h, washed with ethanol and 60° C. water, and dried under vacuum to obtain a crude polymeric microsphere.

(S2) To a conical flask were added 30 mL of deionized water, 5 mL of acrylic acid and 3 g of phenyl vinyl sulfonate, which were stirred evenly for 1 h, added with 4 g of the crude polymeric microsphere, fed with nitrogen for 40 min to remove oxygen, and then sealed. After that, the reaction mixture was exposed to a cobalt source to undergo irradiation, where a radiation absorbed dose was 300 kGy. The reaction system was reacted in a 60° C. water bath for 6 h, and subjected to vacuum filtration to obtain a grafted polymeric microsphere. The grafted polymeric microsphere was washed with deionized water, and dried in a vacuum oven for 24 h to obtain a carboxyl-sulfonic-based polymeric microsphere.

(S3) 1.0 g of the carboxyl-sulfonic-based polymeric microsphere and 0.5 mL of a mCi/μL $^{177}$LuCl$_3$ solution were mixed at room temperature under ultrasonic oscillation for 30 min to obtain an engineered carboxyl-sulfonic-based $^{177}$Lu polymeric microsphere with a diameter of 100 μm.

By means of an intra-arterial catheter or a syringe, the active-targeting delivery of the engineered carboxyl-sulfonic-based $^{177}$Lu polymeric microsphere to a tumor lesion can be achieved.

Example 5 Preparation of Engineered Radioactive Polymeric Microsphere (S1) To 60 mL of deionized water were added 8 g of a styrene monomer, 3 g of SDS and 2 g of vinyltoluene. The reaction mixture was stirred at room temperature for 0.5 h under a nitrogen atmosphere, heated to 50° C., and added with azobisisobutyronitrile. The reaction mixture was reacted under stirring at a constant temperature for 6 h, washed with ethanol and 60° C. water, and dried under vacuum to obtain a crude polymeric microsphere.

(S2) To a conical flask were added 50 mL of deionized water, 5 mL of itaconic acid and 10 g of ethyl styrenesulfonate. The reaction mixture was stirred evenly for 1 h, added with 2 g of the crude polymeric microsphere, fed with nitrogen for 30 min to remove oxygen, and then sealed. After that, the reaction mixture was exposed to an electron beam to undergo irradiation, where a radiation absorbed dose was 280 kGy. The reaction system was reacted in a 80° C. water bath for 6 h, and subjected to vacuum filtration to obtain a grafted polymeric microsphere. The grafted polymeric microsphere was washed with deionized water, and dried in a vacuum oven for 24 h to obtain a carboxyl-sulfonic-based polymeric microsphere.

(S3) 2.0 g of the carboxyl-sulfonic-based polymeric microsphere and 1 mL of a mCi/μL $^{177}$LuCl$_3$ solution were mixed at room temperature under ultrasonic oscillation for 30 min to obtain an engineered carboxyl-sulfonic-based $^{177}$Lu polymeric microsphere with a diameter of 100 μm.

By means of an intra-arterial catheter or a syringe, the active-targeting delivery of the engineered carboxyl-sulfonic-based $^{177}$Lu polymeric microsphere to a tumor lesion can be achieved.

Example 6 Preparation of Engineered Radioactive Polymeric Microsphere (S1) To 80 mL of deionized water were added 15 g of a styrene monomer, 2 g of SDS and 5 g of vinyltoluene. The reaction mixture was stirred at room temperature for h under a nitrogen atmosphere, heated to 70° C., and added with azobisisobutyronitrile. The reaction mixture was reacted under stirring at a constant temperature for 6 h, washed with ethanol and 60° C. water, and dried under vacuum to obtain a crude polymeric microsphere.

(S2) To a conical flask were added 100 mL of deionized water, 10 mL of itaconic acid and 15 g of 2-methacryloyloxyethyl phosphorylcholine. The reaction mixture was stirred evenly for 1 h, added with 4 g of the polymeric microsphere, fed with nitrogen for 30 min to remove oxygen, and then sealed. After that, the reaction mixture was exposed to a cobalt source to undergo irradiation, where a radiation absorbed dose was 500 kGy. The reaction system was reacted in a 80° C. water bath for 6 h, and subjected to vacuum filtration to obtain a grafted polymeric microsphere. The grafted polymeric microsphere was washed with deionized water, and dried in a vacuum oven for 24 h to obtain a carboxyl-phosphorylcholine-based polymeric microsphere.

(S3) 3.0 g of the carboxyl-phosphorylcholine-based polymeric microsphere and 1 mL of a 0.5 mCi/μL $^{177}$LuCl$_3$ solution were mixed at room temperature under ultrasonic oscillation for 30 min to obtain an engineered carboxyl-phosphorylcholine-based $^{177}$Lu polymeric microsphere with a diameter of 120 μm.

By means of an intra-arterial catheter or a syringe, the active-targeting delivery of the engineered carboxyl-phosphorylcholine-based $^{177}$Lu polymeric microsphere to a tumor lesion can be achieved.

Example 7 Preparation of Engineered Radioactive Polymeric Microsphere (S1) To 120 mL of deionized water were added 11 g of a styrene monomer and 5 g of SDS. The reaction mixture was stirred at room temperature for 1 h under a nitrogen atmosphere, heated to 70° C., and added with 1.5 g of benzoyl peroxide. The reaction mixture was reacted under stirring at a constant temperature for 10 h, washed with ethanol and 60° C. water, and dried under vacuum to obtain a crude polymeric microsphere.

(S2) 5 g of the crude polymeric microsphere were exposed to a cobalt source at room temperature under an air atmosphere to undergo a pre-irradiation to obtain a pre-irradiated polymeric microsphere, where a radiation absorbed dose was 300 kGy. To a conical flask were added 60 mL of deionized water, 12 mL of ethyl styrenesulfonate and 10 g of 2-methacryloyloxyethyl phosphorylcholine, which were stirred evenly for 3 h, added with 2 g of the pre-irradiated polymeric microsphere, fed with nitrogen for min to remove oxygen, and then sealed. The reaction system was reacted in a 60° C. water bath for 5 h, and subjected to vacuum filtration to obtain a grafted polymeric microsphere. The grafted polymeric microsphere was washed with deionized water, and dried in a vacuum oven for 24 h to obtain a sulfonic acid-phosphorylcholine-based polymeric microsphere.

(S3) 1.5 g of the sulfonic acid-phosphorylcholine-based polymeric microsphere and 2 mL of a 0.5 mCi/μL $^{177}$LuCl$_3$ solution were mixed at room temperature under ultrasonic oscillation for 30 min to obtain an engineered sulfonic acid-phosphorylcholine-based $^{177}$Lu polymeric microsphere with a diameter of 60 μm.

By means of an intra-arterial catheter or a syringe, the active-targeting delivery of the engineered sulfonic acid-phosphorylcholine-based $^{177}$Lu polymeric microsphere to a tumor lesion can be achieved.

Example 8 Preparation of Engineered Radioactive Polymeric Microsphere (S1) To 65 mL of deionized water were added 7 g of a styrene monomer and 2 g of SDS. The reaction mixture was stirred at room temperature for 1 h under a nitrogen atmosphere, heated to 80° C., and added with 1 g of azobisisobutyronitrile. The reaction mixture was reacted under stirring at a constant temperature for 7 h, washed with ethanol and 60° C. water, and dried under vacuum to obtain a crude polymeric microsphere.

(S2) 2 g of the polymeric microsphere were exposed to a cobalt source at room temperature under an air atmosphere to undergo a pre-irradiation to obtain a pre-irradiated polymeric microsphere, where a radiation absorbed dose was 200 kGy. To a conical flask were added 60 mL of deionized water and 10 g of 2-methacryloyloxyethyl phosphorylcholine, which were stirred evenly for 1 h, added with 1.2 g of the pre-irradiated polymeric microsphere, fed with nitrogen for 30 min to remove oxygen, and then sealed. After that, the reaction system was reacted in a 60° C. water bath for 4 h, and subjected to vacuum filtration to obtain a grafted polymeric microsphere. The grafted polymeric microsphere was washed with deionized water, and dried in a vacuum oven for 24 h to obtain a phosphorylcholine-based polymeric microsphere.

(S3) 0.5 g of the phosphorylcholine-based polymeric microsphere and 1 mL of a mCi/μL $^{177}$LuCl$_3$ solution were mixed at room temperature under ultrasonic oscillation for 30 min to obtain an engineered phosphorylcholine-based $^{177}$Lu polymeric microsphere with a diameter of 60 μm.

By means of an intra-arterial catheter or a syringe, the active-targeting delivery of the engineered phosphorylcholine-based $^{177}$Lu polymeric microsphere to a tumor lesion can be achieved.

Example 9 Preparation of Engineered Radioactive Polymeric Microsphere (S1) To 80 mL of deionized water were added 8 g of a styrene monomer and 1 g of SDS. The reaction mixture was stirred at room temperature for 1 h under a nitrogen atmosphere, heated to 70° C., and added with 1.0 g of azobisisobutyronitrile. The reaction mixture was reacted under stirring at a constant temperature for 6 h, washed with ethanol and 60° C. water, and dried under vacuum to obtain a crude polymeric microsphere.

(S2) 3 g of the crude polymeric microsphere were exposed to a cobalt source at room temperature under an air atmosphere to undergo a pre-irradiation to obtain a pre-irradiated polymeric microsphere, where a radiation absorbed dose was 500 kGy. To a conical flask were added 60 mL of deionized water and 20 g of phenyl vinyl sulfonate, which were stirred evenly for 1 h, added with 1.2 g of the pre-irradiated polymeric microsphere, fed with nitrogen for 30 min to remove oxygen, and then sealed. After that, the reaction system was reacted in a 60° C. water bath for 4 h, and subjected to vacuum filtration to obtain a grafted polymeric microsphere. The grafted polymeric microsphere was washed with deionized water, and dried in a vacuum oven for 24 h to obtain a sulfonic acid-based polymeric microsphere.

(S3) 0.5 g of the sulfonic acid-based polymeric microsphere and 1 mL of a 0.5 mCi/μL $^{177}$LuCl$_3$ solution were mixed at room temperature under ultrasonic oscillation for 30 min to obtain an engineered sulfonic acid-based $^{177}$Lu polymeric microsphere with a diameter of 60 μm.

By means of an intra-arterial catheter or a syringe, the active-targeting delivery of the engineered sulfonic acid-based $^{177}$Lu polymeric microsphere to a tumor lesion can be achieved.

Example 10 Preparation of Engineered Radioactive Polymeric Microsphere (S1) To 100 mL of deionized water were added 12 g of a styrene monomer and 3 g of SDS. The reaction mixture was stirred at room temperature for 1 h under a nitrogen atmosphere, heated to 60° C., and added with 2.0 g of azobisisobutyronitrile. The reaction mixture was reacted under stirring at a constant temperature for 6 h, washed with ethanol and 60° C. water, and dried under vacuum to obtain a crude polymeric microsphere.

(S2) 6 g of the crude polymeric microsphere were exposed to a cobalt source at room temperature under an air atmosphere to undergo a pre-irradiation to obtain a pre-irradiated polymeric microsphere, where a radiation absorbed dose was 200 kGy. To a conical flask were added 80 mL of deionized water and 20 g of vinylphosphonic acid. The reaction mixture was stirred evenly for 1 h, added with 4 g of the pre-irradiated polymeric microsphere, fed with nitrogen for 30 min to remove oxygen, and then sealed, which were reacted in a 60° C. water bath for 6 h, and subjected to vacuum filtration to obtain a grafted polymeric microsphere. The grafted polymeric microsphere was washed with deionized water, and dried in a vacuum oven for 24 h to obtain a phosphate-based polymeric microsphere.

(S3) 1.5 g of the phosphate-based polymeric microsphere and 1 mL of a 0.5 mCi/μL $^{177}$LuCl$_3$ solution were mixed at room temperature under ultrasonic oscillation for 30 min to obtain an engineered phosphate-based $^{177}$Lu polymeric microsphere with a diameter of 60 μm.

By means of an intra-arterial catheter or a syringe, the active-targeting delivery of the engineered phosphate-based $^{177}$Lu polymeric microsphere to a tumor lesion can be achieved.

Diameters of these engineered radioactive polymeric microspheres fabricated in Examples 1-10 were measured by a particle size analyzer (Malvern Mastersizer 3000) to be 10-300 μm, and specific weights of these engineered radioactive polymeric microspheres were measured by gas replacement method to be 1.05-1.25 g/mL, which was close to the specific weight of blood (1.05 g/mL). The gas replacement method was performed through the following steps: (1) testing a volume of an empty pipe; (2) measuring a free volume of the pipe filled with microspheres according to the pressure balance of gas replacement with helium as a medium, calculating a difference between the free volume and the volume of the empty pipe as a volume of the microspheres; (3) calculating a real density (calculated by mass/volume) of the microspheres, namely, the specific weight of the microspheres.

Figure 1:
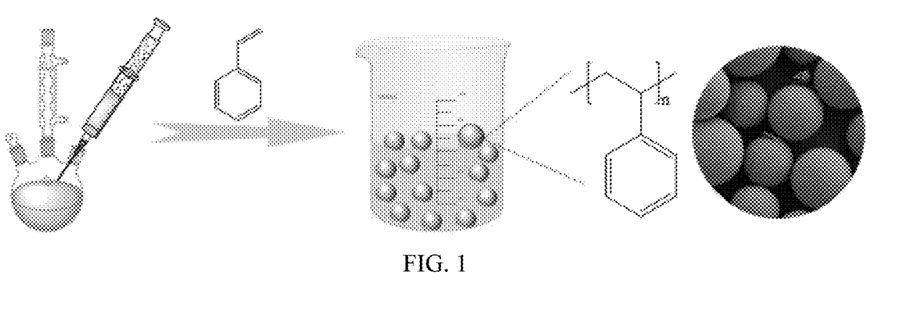
FIG. 1 schematically shows functionalized polymeric microspheres fabricated in Examples 1-10 of the present disclosure.
Figure 2:
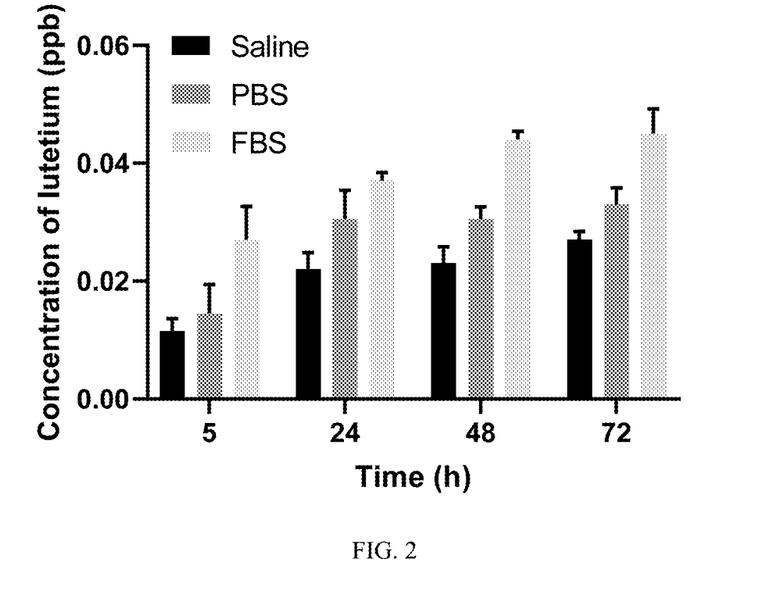
FIG. 2 shows $^{177}$Lu release rates of an engineered $^{177}$Lu-carboxyl-phosphorylcholine polymeric microsphere ($^{177}$Lu-polymeric microsphere) fabricated in Example 3 respectively in normal saline, phosphate-suffered saline (PBS) and fetal bovine serum (FBS)

Experimental Example 1 Radionuclide Release Rate of Phosphorylcholine-Based Polymeric Microsphere Lu release rates of the engineered carboxyl-phosphorylcholine-based $^{177}$Lu polymeric microsphere fabricated in Example 3 in normal saline, PBS and FBS were measured, and results were shown in FIG. 2. Referring to FIG. 2, the engineered $^{177}$Lu carboxyl-phosphorylcholine-based polymeric microsphere had low Lu release rates (much lower than 0.01%) in normal saline, PBS and FBS.

Experimental Example 2 Radionuclide Absorption Rate of Phosphorylcholine-Based Polymeric Microsphere A solution of the engineered carboxyl-phosphorylcholine-based $^{177}$Lu polymeric microsphere fabricated solution in Example 3 was prepared, in which a concentration thereof was 10 mg/mL. The solution was mixed with a 1 mCi $^{177}$Lu solution by ultrasonic for 20 min to prepare a first solution. The solution was mixed with a 1 mCi $^{166}$Ho solution by ultrasonic for 20 min to prepare a second solution. The first solution and the second solution were subjected to centrifugal purification, and added with 1 M sodium citrate as developing solvent, and absorption rates thereof were obtained by thin layer chromatography using rapid silica gel plates. It was indicated that the radionuclide absorption rate of the carboxyl-phosphorylcholine-based polymeric microsphere for $^{177}$Lu and $^{166}$Ho were all above 95.8%.

Figure 3:
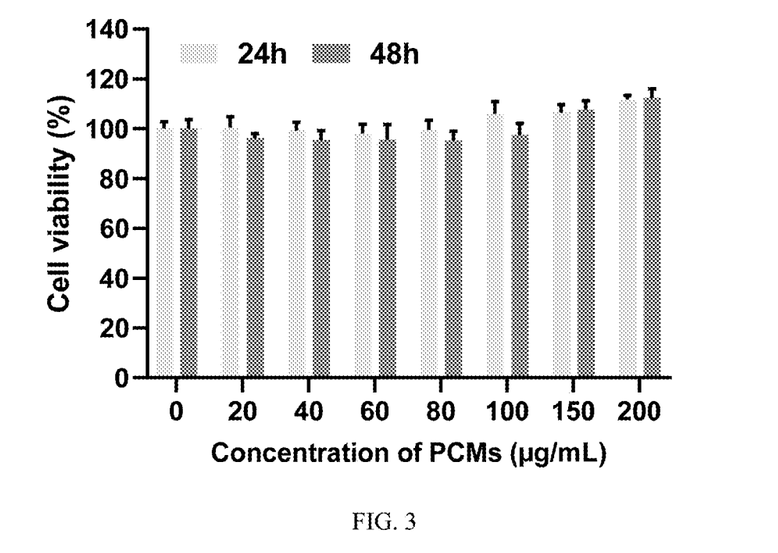
FIG. 3 shows results of cytotoxicity test of the $^{177}$Lu-polymeric microsphere fabricated in Example 3 loaded with LO2 cells.

Experimental Example 3 Cytotoxicity of Phosphorylcholine-Based Polymeric Microsphere to Human Hepatocyte LO2 Cells A series of engineered $^{177}$Lu carboxyl-phosphorylcholine-based polymeric microsphere (fabricated in Example 3) solutions varying in concentration (20, 40, 60, 100, 150 and 200 μg/mL) were prepared, and tested for the cytotoxicity to LO2 cells. The LO2 cells were cultured on a 96-well plate respectively with the pre-sterilized $^{177}$Lu polymeric microsphere solutions varying in concentration, and the cell viability was tested using a cell counting kit-8 (CCK-8) after 1 and 2 days of the culture. Specifically, the LO2 cells were inoculated to a 96-well plate at 5000 cells per well, and incubated for 24 h to allow cell adhesion. Then the medium was replaced with one containing the corresponding concentration of microspheres for another 24-h incubation. A CKK-8 solution was added into the 96-well plate (10 μL of the CKK-8 solution per 100 μL medium), and the 96-well plate was incubated at 37° C. for 1-2 h, and measured with a microplate reader for the absorbance at 450 nm (A450) to calculate the corresponding cell viability. The results were shown in FIG. 3, from which it can be observed that compared with the control group (PBS), the LO2 cells cultured in the phosphorylcholine-based $^{177}$Lu polymeric microsphere solutions (20, 40, 60, 80, 100, 150 and 200 μg/mL) all exhibited normal proliferative activity, indicating that the engineered phosphorylcholine-based $^{177}$Lu polymeric microsphere had great biocompatibility and no cytotoxicity.

Figure 4:
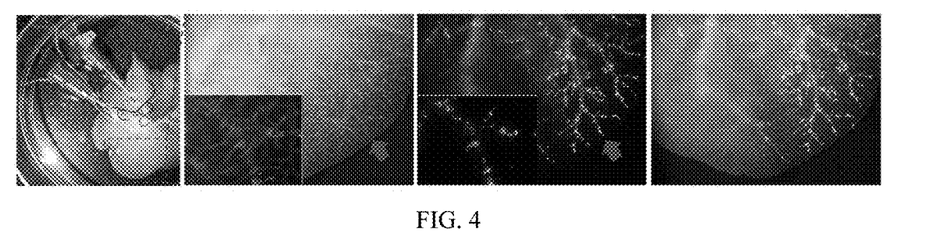
FIG. 4 shows distribution of the $^{177}$Lu-polymeric microsphere fabricated in Example 3 after labeled with fluorescein isothiocyanate (FITC) in normal liver vessels of decellularized rat.

Experimental Example 4 Distribution of Phosphorylcholine-Based Polymeric Microsphere in Decellularized Liver Vessel A decellularized liver model was prepared as follows. Normal liver and NISI liver tumor of a Wistar rat were cut completely. The portal vein and inferior vena cava of the liver were washed with a 0.5-1% SDS solution using a peristaltic pump (speed: 4 mL/min) for 12 h until the liver was semitransparent, followed by washing with normal saline to remove residual SDS. 0.6 mL of a series of phosphorylcholine-based polymeric microsphere with different particle sizes (10 mg/mL, labeled by fluorescein isothiocyanate (FITC)) were slowly injected into the inferior vena cava of the liver by using a 1 mL injector. Images were taken by a fluorescence microscope, and analyzed by Image J, shown as FIG. 4. It indicated that the phosphorylcholine-based polymeric microspheres embolized the distal peripheral vessels, and distributed uniformly, contributing to radiation therapy in tumor-feeding artery bed.

Experimental Example 5

Figure 5:
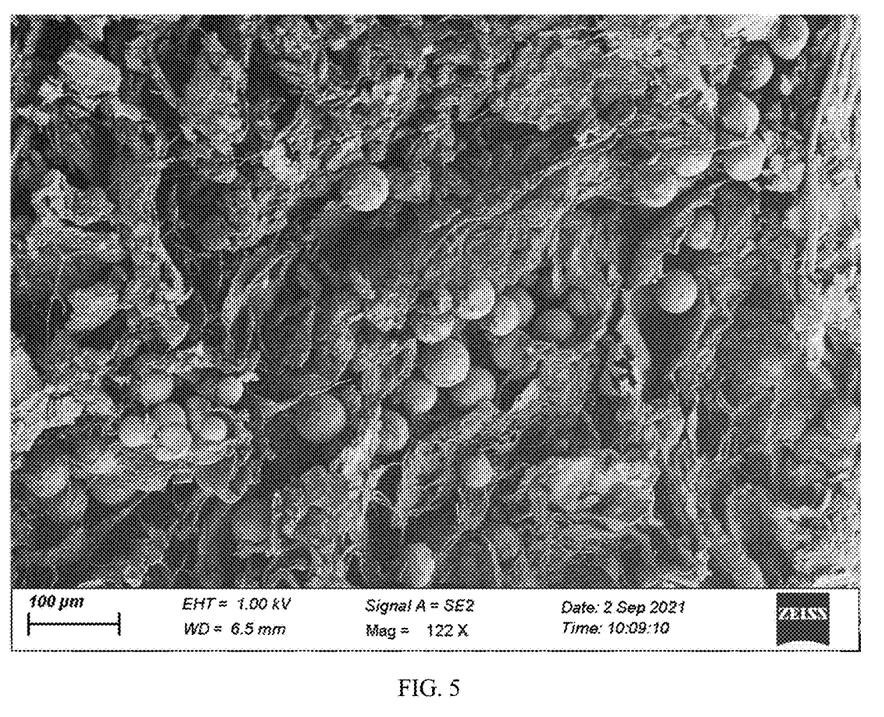
FIG. 5 is a scanning electron microscope (SEM) image showing the distribution of the $^{177}$Lu-polymeric microsphere fabricated in Example 3 in normal liver vessels of the decellularized rat.

The phosphorylcholine-based polymeric microspheres labeled by FITC were subjected to freeze drying, nitrogen embrittlement on the microsphere embolization part. The microsphere embolization part was subjected to metal spraying, and a SEM image shown in FIG. 5 was taken. Referring to FIG. 5, the phosphorylcholine-based polymeric microspheres still maintained a regular spherical shape in the blood vessel after injection and freeze drying, indicating that the phosphorylcholine-based polymeric microspheres had great stability and compression resistance.

Experimental Example 6 In-Vivo Experiment

An in situ hepatocarcinoma-bearing rat model was established as follows.

N1S1 cells were cultivated in Dulbecco's Modified Eagle Medium (DMEM) (10% FBS+penicillin-streptomycin). Once the N1S1 cells proliferated to a desired concentration, the DMEM was centrifuged to collect the N1S1 cells. The N1S1 cells were washed 2-3 times with PBS, and suspended in PBS. A cell concentration was $1 \times 10^6$/mL. An anesthetized SD rat was depilated in the lower left place (liver), fixed in a supine position, and subjected to routine disinfection, draping and laparotomy close to the midline of the abdomen to reduce blood loss. The abdominal muscles and peritoneum were opened in turn, and the left lobe of the liver was exposed from the incision with an iodine swab. 100-200 μL of the N1S1 cell suspension was slowly injected into the liver tissue (left lobe of liver, right down the middle) using a single-use sterile insulin syringe. Since the liver stopped bleeding, the injector was slowly removed. Finally, the incision was subjected to hemostasis with disinfect swab, fixed with gelatin sponge, sutured in turn, and disinfected with iodophor. About 1 week later, MRI was performed to determine whether the in situ hepatocarcinoma-bearing rat model was successfully established.

The engineered carboxyl-phosphorylcholine-based $^{177}$Lu polymeric microsphere (fabricated in Example 3) was considered as an experimental group to carry out TARE, and a control group was not subjected to TARE. Regarding the experimental group, the thoracoabdominal region of the in situ liver cancer rat was dissected, and the hepatic artery was picked out. 300 μCi $^{177}$Lu phosphorylcholine-based polymeric microsphere (1 mg/mL) were injected into a tumor feeding artery by using a 1 mL injector with injection speed of 0.2 mL/min. The embolization was stopped when the tumor vessels were completely embolized or regurgitation occurred, followed by ligating the wound.

Figure 6:
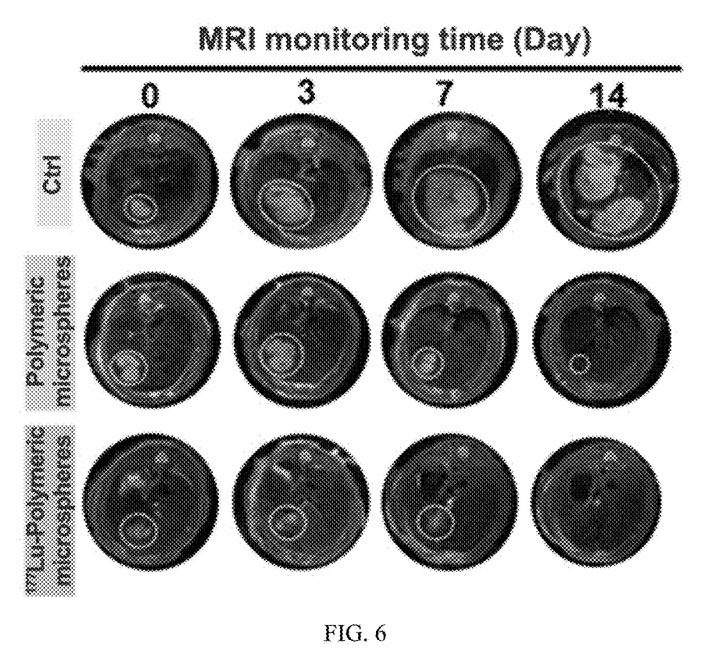
FIG. 6 shows magnetic resonance imaging (MM) images of hepatocarcinoma-bearing rat groups after in situ targeted therapy through trans-arterial embolization (TAE) with the $^{177}$Lu-polymeric microsphere fabricated in Example 3, where the first row: MM images of an untreated hepatocarcinoma-bearing rat group (Control group, Ctrl) after 0, 3, 7 and 14 days; the second row: MM images of a hepatocarcinoma-bearing rat group treated by in-situ TAE with a carboxyl-phosphorylcholine-functionalized polymeric microsphere after 0, 3, 7 and 14 days of the treatment (blank polymeric microsphere group); and the third row: MRI images of a hepatocarcinoma-bearing rat group (Experimental group) after 0, 3, 7 and 14 days of in-situ targeted therapy with the $^{177}$Lu-polymeric microsphere through TAE.

The experimental group and the control group were subjected to MRI after 0, 3, 7 and 14 days treating, and results were shown in FIG. 6. Referring to FIG. 6, the liver tumor of the rat injected with the $^{177}$Lu-polymeric microsphere fabricated in Example 3 through TAE become smaller and necrotic after 14 days, indicating that embolization-radiotherapy-combining treatment was effective to the in situ hepatocarcinoma-bearing rat model. The liver tumor of the control group was significantly enlarged after 14 days.

The engineered $^{177}$Lu phosphorylcholine-based polymeric microsphere provided herein can realize effective embolization-radiotherapy-combining treatment in the in situ hepatocarcinoma-bearing rat model through TARE. The phosphorylcholine-based $^{177}$Lu polymeric microsphere can be used in radiotherapy for hepatocarcinoma and radiographic diagnosis.

In summary, the engineered radioactive polymeric microsphere provided herein satisfies requirements of intravascular brachytherapy, and has the following properties. (1) It has high mechanical strength, and can be transported in the blood capillary without decomposition. (2) It has high chemical stability, and the radionuclide of the polymeric microsphere is not easy to fall off, not swallowed by macrophages, and not decomposed by radiation. (3) It has an appropriate density, and is thus easy to prepare a uniform suspension. (4) The labelled nuclide can be used to treat tumor effectively, and can be used for nuclear medicine imaging diagnosis, and has appropriate half-life. (5) It has great biocompatibility and is non-toxic, which ensure the safety when entering human body. (6) It is simple to prepare, environmental and low-cost, and is possible to realize large scale production.

Mentioned above are merely preferred embodiments of this disclosure, which are not intended to limit the scope of the present disclosure. It should be understood that any changes, replacements and improvements made by those killed in the art without departing from the spirit of this disclosure should fall within the scope of the present disclosure defined by the appended claims.

What is claimed is:

1. A method for preparing an engineered radioactive polymeric microsphere, comprising:
adding 10 g of a styrene monomer and 1 g of sodium dodecyl sulfate (SDS) to 20 mL of deionized water, followed by stirring at room temperature in a nitrogen atmosphere for 2 h to obtain a first reaction mixture;
heating the first reaction mixture to 50° C. and adding 2 g of dibenzoyl peroxide to the first reaction mixture, followed by reaction under stirring at a constant temperature for 6 h to obtain a second reaction mixture; and
subjecting the second reaction mixture to washing with ethanol and 60° C. water, and vacuum drying to obtain a crude polymeric microsphere;
weighing 3 g of the crude polymeric microsphere followed by irradiation in the exposure to a cobalt source at room temperature under an air atmosphere to obtain an irradiated polymeric microsphere, wherein a radiation absorbed dose is 100 kGy; adding 60 mL of deionized water and 10 mL of vinylphosphonic acid to a conical flask followed by stirring for 1 h to obtain a vinylphosphonic acid solution; adding 3 g of the irradiated polymeric microsphere to the vinylphosphonic acid solution followed by nitrogen feeding for 20 min to remove oxygen and sealing to obtain a third reaction mixture; subjecting the third reaction mixture to reaction in a 55° C. water bath for 3 h and vacuum filtration to obtain a grafted polymeric microsphere; and subjecting the grafted polymeric microsphere to washing with deionized water and drying in a vacuum oven for 24 h to obtain a phosphate-based polymeric microsphere; and
mixing 0.5 g of the phosphate-based polymeric microsphere with 1 mL of a 0.5 mCi/μL $^{177}$LuCl$_3$ solution at room temperature under ultrasonic oscillation for 30 min to obtain an engineered phosphate-based $^{177}$Lu polymeric microsphere with a diameter of 40 μm.

2. A method for preparing an engineered radioactive polymeric microsphere, comprising:

adding 20 g of a styrene monomer and 3 g of sodium dodecyl sulfate (SDS) to 50 mL of ethanol, followed by stirring at room temperature in a helium atmosphere for 1 h to obtain a first reaction mixture;

heating the first reaction mixture to 60° C. and adding 0.5 g of azobisisobutyronitrile to the first reaction mixture, followed by reaction under stirring at a constant temperature for 4 h to obtain a second reaction mixture; and subjecting the second reaction mixture to washing with ethanol and 60° C. water, and vacuum drying to obtain a crude polymeric microsphere;

weighing 5 g of the crude polymeric microsphere followed by irradiation in the exposure to an electron beam at room temperature under an air atmosphere to obtain an irradiated polymeric microsphere, wherein a radiation absorbed dose is 300 kGy; adding 50 mL of deionized water, 10 mL of vinyl pyrrolidone and 15 mL of 4-vinylaniline to a conical flask followed by stirring for 2 h to obtain a mixed solution; adding 4 g of the irradiated polymeric microsphere to the mixed solution followed by nitrogen feeding for 40 min to remove oxygen and sealing to obtain a third reaction mixture; subjecting the third reaction mixture to reaction in a 65° C. water bath for 6 h and vacuum filtration to obtain a grafted polymeric microsphere; and subjecting the grafted polymeric microsphere to washing with deionized water and drying in a vacuum oven for 24 h to obtain an amino-based polymeric microsphere; and mixing 2.0 g of the amino-based polymeric microsphere with 1 mL of a 0.5 mCi/μL $^{177}$LuCl$_3$ solution at room temperature under ultrasonic oscillation for 30 min to obtain an engineered amino-based $^{177}$Lu polymeric microsphere with a diameter of 80 μm.

3. A method for preparing an engineered radioactive polymeric microsphere, comprising:

adding 12 g of a styrene monomer and 4 g of sodium dodecyl sulfate (SDS) to 80 mL of deionized water, followed by stirring at room temperature in a nitrogen atmosphere for 1 h to obtain a first reaction mixture;

heating the first reaction mixture to 50° C. and adding 1.2 g of azobisisobutyronitrile to the first reaction mixture, followed by reaction under stirring at a constant temperature for 3 h to obtain a second reaction mixture; and subjecting the second reaction mixture to washing with ethanol and 60° C. water, and vacuum drying to obtain a crude polymeric microsphere;

weighing 4 g of the crude polymeric microsphere followed by irradiation in the exposure to an electron beam at room temperature under an air atmosphere to obtain an irradiated polymeric microsphere, wherein a radiation absorbed dose is 200 kGy; adding 50 mL of deionized water, 10 mL of acrylic acid and 10 g of 2-methacryloyloxyethyl phosphorylcholine to a conical flask followed by stirring for 2 h to obtain a mixed solution; adding 2 g of the irradiated polymeric microsphere to the mixed solution followed by nitrogen feeding for 30 min to remove oxygen and sealing to obtain a third reaction mixture; subjecting the third reaction mixture to reaction in a water bath for 5 h and vacuum filtration to obtain a grafted polymeric microsphere; and subjecting the grafted polymeric microsphere to washing with deionized water and drying in a vacuum oven for 24 h to obtain a carboxyl-phosphorylcholine-based polymeric microsphere; and mixing 1.2 g of the carboxyl-phosphorylcholine-based polymeric microsphere with 2 mL of a 0.5 mCi/μL $^{177}$LuCl$_3$ solution at room temperature under ultrasonic oscillation for 30 min to obtain an engineered carboxyl-phosphorylcholine-based $^{177}$Lu polymeric microsphere with a diameter of 60 μm.

\* \* \* \* \*